(12) United States Patent
Hissink et al.

(10) Patent No.: US 10,507,260 B2
(45) Date of Patent: Dec. 17, 2019

(54) BIOMEDICAL FOAMS

(71) Applicant: Stryker European Holdings I, LLC, Kalamazoo, MI (US)

(72) Inventors: Catharina Everdina Hissink, Groningen (NL); Theodorus Adrianus Cornelius Flipsen, Groningen (NL); Johan Zuidema, Groningen (NL); Linda Joan Gibcus, Groningen (NL)

(73) Assignee: Stryker European Holdings I, LLC, Kalamazoo, MI (US)

( * ) Notice: Subject to any disclaimer, the term of this patent is extended or adjusted under 35 U.S.C. 154(b) by 631 days.

(21) Appl. No.: 14/695,174

(22) Filed: Apr. 24, 2015

(65) Prior Publication Data

US 2015/0273102 A1 Oct. 1, 2015

Related U.S. Application Data

(60) Division of application No. 11/178,259, filed on Jul. 8, 2005, now Pat. No. 9,610,377, which is a
(Continued)

(30) Foreign Application Priority Data

Jan. 9, 2003 (EP) .................................... 03075065

(51) Int. Cl.
*A61L 15/26* (2006.01)
*A61L 15/64* (2006.01)
(Continued)

(52) U.S. Cl.
CPC ............. *A61L 15/26* (2013.01); *A61L 15/425* (2013.01); *A61L 15/64* (2013.01);
(Continued)

(58) Field of Classification Search
CPC ...... A61L 15/26; A61L 15/64; A61L 26/0085; A61L 15/425; A61L 24/046;
(Continued)

(56) References Cited

U.S. PATENT DOCUMENTS 3,875,937 A 4/1975 Schmitt et al.
3,902,497 A 9/1975 Casey
(Continued)

FOREIGN PATENT DOCUMENTS

EP 0295055 A2 12/1988
EP 0335669 A2 10/1989
(Continued)

OTHER PUBLICATIONS

Office Action issued for corresponding Japanese Patent Application No. 2011-172910, dated Jun. 7, 2013.
(Continued)

*Primary Examiner* — Rachael E Bredefeld
(74) *Attorney, Agent, or Firm* — Howard & Howard Attorneys PLLC

(57) ABSTRACT

The invention relates, generally, to porous absorbent materials which are suitable for packing antrums or other cavities of the human or animal body. More particularly, it relates to hydrophilic biodegradable foams, which may be used e.g. in the form of a plug or tampon, for instance for controlling bleeding, wound closure, prevent tissue adhesion and/or support tissue regeneration. The invention provides an absorbent foam, suitable for packing antrums or other cavities of the human or animal body, comprising a biodegradable synthetic polymer, which polymer preferably comprises —C(O)—O— groups in the backbone of the polymer, for instance polyurethane and/or polyester units combined with polyethers.

19 Claims, 5 Drawing Sheets

Related U.S. Application Data continuation of application No. PCT/NL2004/000010, filed on Jan. 8, 2004.

(51) Int. Cl.

| | | |
|---|---|---|
| A61L 26/00 | (2006.01) | |
| A61L 15/42 | (2006.01) | |
| A61L 24/04 | (2006.01) | |
| A61L 24/00 | (2006.01) | |
| C08G 18/40 | (2006.01) | |
| C08G 18/08 | (2006.01) | |
| C08G 18/32 | (2006.01) | |
| C08G 18/73 | (2006.01) | |
| C08G 18/10 | (2006.01) | |
| C08G 18/42 | (2006.01) | |
| C08L 75/04 | (2006.01) | |
| C08G 101/00 | (2006.01) | |

(52) U.S. Cl.
CPC ......... *A61L 24/0036* (2013.01); *A61L 24/046* (2013.01); *A61L 26/0085* (2013.01); *C08G 18/10* (2013.01); *C08G 18/14* (2013.01); *C08G 18/3206* (2013.01); *C08G 18/4018* (2013.01); *C08G 18/4277* (2013.01); *C08G 18/73* (2013.01); *C08L 75/04* (2013.01); *C08G 2101/0083* (2013.01); *C08G 2230/00* (2013.01)

(58) Field of Classification Search
CPC . A61L 24/0036; C08G 18/4018; C08G 18/14; C08G 18/3206; C08G 18/73; C08G 18/4277; C08G 18/10; C08G 2230/00; C08L 75/04

See application file for complete search history.

(56) References Cited

U.S. PATENT DOCUMENTS

| | | | |
|---|---|---|---|
| 3,903,232 A | 9/1975 | Wood et al. | |
| 3,961,629 A | 6/1976 | Richter et al. | |
| 4,550,126 A | 10/1985 | Lorenz | |
| 5,968,075 A | 10/1999 | Wood | |
| 2001/0043913 A1 | 11/2001 | Spaans et al. | |
| 2003/0236573 A1* | 12/2003 | Evans | A61L 27/12 623/23.58 |

FOREIGN PATENT DOCUMENTS

| | | |
|---|---|---|
| JP | H-1195862 A | 4/1999 |
| WO | WO9013320 | 11/1990 |
| WO | WO9964491 | 12/1999 |

OTHER PUBLICATIONS

English Translation of Office Action issued for corresponding Japanese Patent Application No. 2011-172910 dated Jun. 7, 2013.
Office Action issued for corresponding Japanese Patent Application No. 2006-500726 dated Sep. 11, 2013.
English Translation of Office Action issued for corresponding Japanese Patent Application No. 2006-500726, dated Sep. 11, 2013.

* cited by examiner

BIOMEDICAL FOAMS

CROSS-REFERENCE TO RELATED APPLICATIONS

This application is a division of U.S. patent application Ser. No. 11/178,259, filed Jul. 8, 2005, and entitled "Biomedical Foams" which is a continuation of PCT/NL04/00010, filed on Jan. 8, 2004, which claims priority to European Patent Application No. 03075065.7, the entirety of each is hereby incorporated by reference.

FIELD OF THE INVENTION

The invention relates, generally, to biodegradable porous absorbent materials which are suitable for packing antrums or cavities of the human or animal body. More particularly, it relates to biodegradable absorbent foams, which may be used e.g. in the form of a plug, tampon or sheet, for instance for controlling bleeding (a haemostatic sponge), wound closure and/or support tissue regeneration.

DESCRIPTION OF THE PRIOR ART

Nasal packing is the application of packs to the nasal cavities. The most common purpose of nasal packing is to control bleeding following surgery to the septum or nasal reconstruction, to prevent synechiae (adhesion) or restenosis and to treat epistaxis (nose bleeding). Packing is also used to provide support to the septum after surgery.

In cases of septoplasty and rhinoplasty surgery, conventional non-biodegradable packings are frequently removed within 24-48 hours following surgery. In the case of epistaxis, packing is left in for extended periods of time to promote healing and to prevent the patient from touching and accidentally interfering with the recovery of the wound. The packing may be left in the nose for as long as 7-10 days. If the wound is high up in the nasal cavity, packings treated with petrolatum and/or antibiotics are sometimes used. In the art, biodurable wound dressings are used for nasal packing. These biodurable packs have to be removed after several days as described above. Removing the pack when the wound is still fresh may damage the nasal cavity again and is associated with patient discomfort. In some cases this is even associated with a vaso-vagal reaction followed by fainting of the patient.

Numerous materials have been proposed in the prior art for use as dental and biomedical foams for absorbing or removing body fluids. Conventional packs consisting of gauze or cotton have several disadvantages: the fluid absorption capacity of the material is relatively low, the structure is relatively fragile and individual threads or fibres may break off, erroneous failure to remove the material from the body after internal surgery may lead to serious complications and the material is relatively expensive.

Certain hydrophilic synthetic materials intended for biomedical applications have improved properties when compared to conventional materials when it comes to absorption capacities and physico-mechanical properties. Examples of such material are the cross-linked polyurethane-based hydrogels as disclosed in e.g. U.S. Pat. Nos. 3,903,232, 3,961,629, 4,550,126 and EP-A-0 335 669. However, these materials are biodurable and not biodegradable.

This lack of biodegradability makes such materials less suitable for use in body cavities during surgery, since there is always a possibility that the foam is left accidentally in the body. Furthermore, removing non-biodegradable foams after application in a natural body orifice may be very uncomfortable for a patient and may open up the wound and/or lead to additional scarring of the tissue.

In order to prevent these undesired effects, biodegradable sponges or absorbing foams comprising materials of a natural source such as gelatine, proteins (collagen), chitin, cellulose or polysaccharides have been suggested. However, all of these materials lack the required mechanical strength. For example, the haemostatic sponge of denatured gelatin of WO 90/13320 does not have sufficient mechanical strength to stop a severe nose-bleeding, because the compression strength of the material in the wet condition is too low and the sponge liquefies too fast after being applied in the nasal cavity. Furthermore, properties of natural polymers are difficult to control; they may have batch to batch variations, and they are generally more expensive than synthetic materials. Also, biodegradable material of natural sources, especially of animal origin, is not preferred, because of the biological hazards associated with its use.

Synthetic surgical dressings that are absorbable by the body have been disclosed in a few patent applications. U.S. Pat. Nos. 3,902,497 and 3,875,937 disclose surgical dressings of bio-absorbable polymers of polyglycolic acid (PGA). Such materials are, although useful in other applications, not useful in applications where sufficient counter pressure from the foam is required, such as in nose-bleeding, because the material is quite hard and brittle and is not resilient. Therefore, the physical properties of the PGA-based foams are not suited for application in many medical situations. Moreover, the PGA material is not sufficiently hydrophilic to absorb the blood during severe bleeding. In order to control severe bleeding, foams preferably exhibit high absorption capacities due to the hydrophilic nature of the material.

The need for synthetic absorbable sponges or absorbent foams that can be left in the wound is now well recognized. Requirements of such foams are a) a high (fluid) absorption capacity, particularly for blood, b) rapid absorption of fluid, c) strength to be readily handled in surgical procedures, d) conformable so as to fit into any topography or space, e) maintenance of mechanical properties, such as resilience, for a specific period of time during or after surgery or after application of the foam, and f) soft so as to avoid injury to sensitive tissues. In some instances, the softness of the foam may be increased by wetting of the foam. Therefore, the absorbing foam should also have enough mechanical strength and elasticity in the wet condition.

There is a need for bio-compatible, biodegradable synthetic foams that can be applied as medical sponges or as wound dressings with improved physical and mechanical properties. It is a particular objective of the present invention to overcome the drawbacks and the problems associated with the sponges and absorbent foams of the prior art and to provide a foam material that is biodegradable, that is able to absorb liquids or body fluids and that has improved mechanical properties, such as a high elasticity, even when wet.

SUMMARY OF THE INVENTION

It has now surprisingly been found that a biodegradable absorbent foam comprising a phase-separated polymer consisting of an amorphous segment and a crystalline segment and wherein at least said amorphous segment comprises a hydrophilic segment provides improved physical and mechanical properties for packing antrums or other cavities of the human or animal body and does not suffer from the disadvantages of the sponges of the prior art.

According to the present invention, the amorphous segment must comprise a hydrophilic segment. This amorphous segment, also called the amorphous phase in the art, is amorphous when packed in an antrum or other cavity of the human or animal body, i.a. when wet, in the wet state, despite the fact that it may comprise a crystalline polyether. This means that, in the dry state, said crystalline polyether may provide the amorphous phase of the polymer with partially crystalline properties. The performance of the foam in the packed state determines the characteristics of the foam: in the packed state, the foam of the invention is comprised of an amorphous hydrophilic soft segment or phase and a crystalline hard segment or phase.

The phase-separated character of the polymer from which the foam of the invention is comprised, provides the material with very suitable characteristics. The presence of hydrophilic segment or group in the amorphous phase of the polymer from which the foam of the invention is comprised further provides said foam with required characteristics such as the capacity to absorb aqueous liquids and being readily biodegradable.

Hydrophilic groups may also be present in the hard segment of the polymer, but the presence of hydrophilic groups in the hard segment should not result in immediate disintegration of the foam when placed in contact with fluids. Essentially, the crystalline hard segment or phase must provide the foam with rigidity, keep the foam intact and prevent swelling of the foam when placed in contact with fluids. Also, a foam of the invention may comprise more than one amorphous segment or phase.

In a first aspect, therefore, the present invention provides a biodegradable absorbent foam, suitable for packing antrums or other cavities of the human or animal body, comprising a phase-separated polymer consisting of an amorphous segment and a crystalline segment and wherein said amorphous segment comprises a hydrophilic segment.

In one embodiment of said aspect, a biodegradable absorbent foam is provided which foam comprises a polymer of the formula:

$$-[R-Q^1[-R'-Z^1-[R''-Z^2-R'-Z^3]_p-R''-Z^1]_q-R'-Q^2]-_n \quad (I),$$

wherein R is selected from one or more aliphatic polyesters, polyetheresters, polyethers, polyanhydrides and/or polycarbonates, and at least one R comprises a hydrophilic segment, R' and R" are independently $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O (e.g. ether, ester, carbonate and/or anhydride groups) in the alkylene chain, $Z^1$-$Z^4$ are independently amide, urea or urethane, $Q^1$ and $Q^2$ are independently urea, urethane, amide, carbonate, ester or anhydride, n is an integer from 5-500, p and q are independent 0 or 1, provided that when q is 0, R is a mixture of at least one crystalline polyester, polyetherester or polyanhydride segment and at least one amorphous aliphatic polyester, polyether, polyanhydride and/or polycarbonate segment. The O containing moieties in the alkylene chain, if present, are preferably hydrophilic groups, in particular ether groups, since such hydrophilic groups can provide a reduced degradation time to the polymer, which may be desirable for the polymer's use in implants.

The simplest form of the polymer from which a foam of the invention may be comprised is of the formula: —R-$Q^1$-R'-$Q^2$-, i.e. when q=0.

According to the present invention, the amorphous segment is comprised in the —R— part of the polymer according to formula (I). In case q=1, the $Q^1[-R'-Z^1-[R''-Z^2-R'-Z^3]_p-R''-Z^4]_q-R'-Q^2$ part of the polymer according to formula (I) represents the crystalline segment. In this particular case the amorphous and crystalline segments are alternating, thus providing the hard segment with a uniform block-length.

As described above, R may represent a mixture of two or more different types of aliphatic polyesters, polyetheresters, polyethers, polyanhydrides and/or polycarbonates, which mixture comprises both amorphous and crystalline types, so that both are comprised in a foam of the invention. In the case that a mixture of amorphous and crystalline types of R segments are provided in a polymer according to the formula (I), at least one hydrophilic segment is provided in at least one amorphous R segment.

In a polymer according to the formula (I), $Q^1$ and $Q^2$ may be selected from amide, urea, urethane ester, carbonate or anhydride groups, whereas $Z^1$ through $Z^4$ should be chosen from amide, urea or urethane groups so that at least 4 hydrogen bond forming groups are present in a row in the crystalline segment. The group R in —$Z^2$—R'—$Z^3$— may be different or similar to R' in -$Q^1$-R'—$Z^1$— or —$Z^4$—R'-$Q^2$-.

As stated, R comprises a hydrophilic segment and such a hydrophilic segment can very suitably be an ether segment, such as a polyether segment derivable from such polyether compounds as polyethyleneglycol, polypropyleneglycol or polybutyleneglycol. Also, a hydrophilic segment comprised in R may be derived from polypeptide, poly(vinyl alcohol), poly(vinylpyrrolidone) or poly(hydroxymethylmethacrylate). A hydrophilic segment is preferably a polyether.

In an alternative embodiment, a biodegradable absorbent foam is provided by the present invention, which foam comprises a polymer of the formula:

$$-[R-Q^1-R'''-Q^2-]_n \quad (II)$$

wherein R, $Q^1$, $Q^2$ and n are as described above, $Q^1$ and $Q^2$ are independently, urea, urethane, amide, carbonate, ester or anhydride, preferably urea, urethane or amide, R''' is chosen from R, R' or R" as described above, provided that when R''' is R' or R", R is a mixture of at least one crystalline polyester, polyetherester or polyanhydride and at least one amorphous aliphatic polyester, polyether, polyanhydride and/or polycarbonate. When R''' is R, at least one crystalline polyester, polyetherester or polyanhydride and at least one amorphous aliphatic polyester, polyether, polyanhydride and/or polycarbonate is provided in said polymer. Again, a hydrophilic segment is then provided in said amorphous segment of the phase-separated polymer and the amorphous and crystalline segments are alternating.

In a further aspect, the present invention provides a phase-separated biodegradable polymer of the formula (I) as defined above.

In yet another aspect, the present invention provides a method for preparing a phase-separated biodegradable polymer of the formula (I) according to the invention, comprising reacting:

one or more pre-polymers of the formula:

$$A-R-A' \quad (III),$$

with one or more diisocyanates of the formula:

$$O=C=N-R'-N=C=O \quad (IV)$$

and optionally one or more chain extenders of the formula:

$$B-R''-B' \quad (V)$$

wherein R, R', and R" are as defined in formula (I), and A, A', B and B' are independently selected from hydroxyl, carboxyl or amine. Preferable, the chain extension reaction with (reaction products of) above compounds (III), (IV) and (V) are performed in a solvent, more preferably in 1,4-dioxane or trioxane, even more preferably 1,4-dioxane. In an even more preferred embodiment, a reaction between compounds (III) and (IV) is performed in bulk after which a so called chain extension reaction is performed with compound (V) in a solvent.

In an alternative of this embodiment, a reaction between compounds (IV) and (V) is performed in bulk after which a so called chain extension reaction is performed with compound (III) in a solvent. By choosing the sequence of reacting the compounds of the formulas (III), (IV) and (V) with each other, i.e., first (III) and (IV) and then (V), or, alternatively, first (IV) and (V) and then (III), the organization and properties of the resulting polymer can be adapted and controlled.

In order to provide for phase-separated polymers with even better properties the sequence of reacting the compounds of the formulas (III), (IV) and (V) with each other can be further adapted, for instance, by first reacting the compounds of the formulas (IV) and (V) to form an intermediate complex. Depending on the molar ratio's of the compounds (IV) and (V) used (i.e. one of the compounds should be present in excess over the other), either a diisocyanate according to the formula:

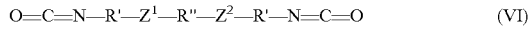

O=C=N—R'—Z¹—R"—Z²—R'—N=C=O       (VI)

is formed, with R', R", Z¹ and Z² as defined above,
or a compound with end-groups of hydroxyl, carboxyl or amine, i.e. a compound of the formula:

B—R"—Z¹—R'—Z²—R'—B'       (VII), wherein R', R", Z¹, Z², B and B' are as defined above.
The compound (VI), i.e. the intermediate diisocyanate complex, can directly be used in a reaction with the compound of the formula (III), whereas the compound (VII), i.e. the intermediate compound with end-groups of hydroxyl, carboxyl or amine, is again reacted with excess diisocyanate of the formula (IV) to yield a diisocyanate of the formula:

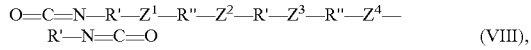

O=C=N—R'—Z¹—R"—Z²—R'—Z³—R"—Z⁴—
R'—N=C=O       (VIII)

wherein R', R" and Z¹-Z⁴ are as defined above, which compound (VIII) is then used in a reaction with the compound (III) to yield a polymer of the invention.

The result of this latter method is a phase-separated biodegradable polymer of the formula (I) wherein the elements R' and R" are comprised in the alternating form of a R'—R"—R'—R"—R' segment, and wherein the elements R' and R" are linked by various types of chemical bonds Z.

This polymeric structure can also be prepared by an alternative method wherein a compound of the formula (IV) is reacted with excess compound of the formula (V) to yield an intermediate compound of the formula (VII) followed by reacting this intermediate compound with another intermediate compound of the formula:

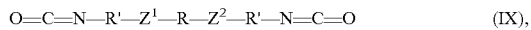

O=C=N—R'—Z¹—R—Z²—R'—N=C=O       (IX), generated by reacting the compound of the formula (III) with an excess of the compound of the formula (IV). The reaction between a compound of the formula (VII) with a compound of the formula (IX) will result in the formation of a polymeric compound with the segment sequence —R'—R—R'—R"—R'—R"—.

A polymer of formula (I) and with q=0 (or formula (II) with R'''=R'), can be obtained by a chain-extension reaction of at least two compounds of formula (III) with a compound of formula (IV) provided that R is a mixture of at least one crystalline polyester, polyetherester or polyanhydride segment and at least one amorphous aliphatic polyester, polyether, polyanhydride and/or polycarbonate segment containing a hydrophilic group.

The polymer of the present invention may be produced in bulk, or, more preferably, it may be produced in a solvent. A very suitable such solvent is 1,4-dioxane or trioxane. The advantage of producing a polymer of the present invention in a solvent is that a very advantageous starting material is thus provided for the preparation of a foam of the invention. This starting material is already present in the form of a solution, and no time-consuming dissolution of polymers in solvents needs to be accomplished. Most preferred is the use of the solvent 1,4-dioxane.

In another aspect, the present invention provides a method for preparing a foam of the invention, comprising providing a solution of a phase-separated polymer, which polymer comprises an amorphous segment and a crystalline segment and wherein at least the amorphous segment comprises a hydrophilic segment, in 1,4-dioxane or trioxane, freezing the solution, and subliming the solvent by freeze-drying. Freeze drying may be performed by standard methods known in the art.

In an alternative embodiment, a foam of the invention may be prepared by a method comprising providing a phase-separated biodegradable polymer and forming said polymer into a foam of the invention, for example, by using a blowing agent in a extrusion method as known in the art. Such an extrusion method may for instance comprise the melting of said polymer and the extrusion of the melt thus formed into a foam by the aid of a gas, preferably a gas such as carbon dioxide.

In yet another alternative embodiment, a foam of the invention may for instance be prepared by a method comprising preparing a phase-separated biodegradable polymer of the formula (I) by reacting a diisocyanate molecule of the formula (IV), or one of the intermediate diisocyanate compounds (VI), (VIII) or (IX) as described above, with a dicarboxylic acid or hydroxycarboxylic acid of the formula (III) and/or (V), optionally in combination with a di-hydroxyl pre-polymer of the formula (III) and optionally in the presence of water, and allowing in situ generation of carbon dioxide during the completion of the polymerization reaction. The ratio of isocyanate groups to carboxyl and hydroxy groups (including water) should preferably be close to 1.

In a preferred embodiment, however, a method for preparing a biodegradable absorbent foam, suitable for packing antrums or other cavities of the human or animal body, comprises preparing a polymer according to the invention in 1,4-dioxane or trioxane, diluting the polymer solution during polymerization with the solvent, freezing the reaction mixture, and subliming the solvent, as stated above.

In yet another embodiment, a foam of the invention may be prepared by a method comprising preparing a phase-separated biodegradable polymer of the formula (II) by reacting at least two different compounds according to formula (III) with each other. In this case R comprises at least one hydrophilic segment and at least one compound according to formula (III) provides a crystalline segment, and at least a second compound according to formula (III) provides an amorphous segment, said at least one hydrophilic segment being provided in said amorphous segment (R''' is R in formula (II)). Alternatively, compounds of formula (III) can be reacted with a compound of the formula (V) or (VII) and in combination with a chain extension reaction in the presence of an activator, such as N-hydroxysuccinimide or derivatives, carbonyldiimidazole, aldehydes, maleimides or dicycloxexyl carbodiimide (DCC). Such reactions are well known in the art.

In a further aspect, the present invention provides a biodegradable synthetic absorbent foam, suitable for packing antrums or other cavities of the human or animal body, obtainable by a method of the present invention.

In a final aspect, the present invention relates to the use of a foam according to the invention as a haemostatic sponge, as a wound dressing material, as a packing for antrums or other cavities of the human or animal body, including dental packs, or as a drug delivery vehicle, as well as to the use of a phase-separated biodegradable polymer of the invention for the manufacture of a foam of the invention.

DETAILED DESCRIPTION OF THE INVENTION

Figure 1:
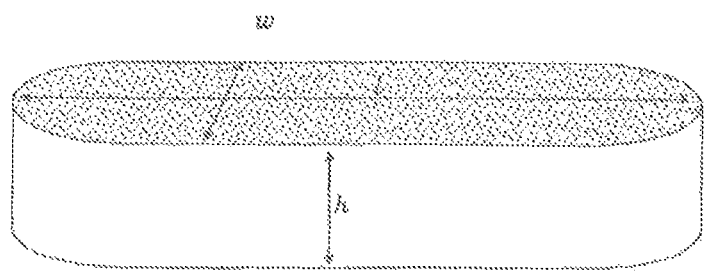
FIG. 1 shows schematically suitable shape and dimensions of a polyethyleneglycol-containing polyurethane foam according to the invention for intended use as a nasal dressing.

The term "sponge" is understood to mean a porous structure characterized in that the structure is reticulate and has an inner surface considerably larger than its outer surface, that it contains hollow spaces (pores) within the reticulate structure and that it can absorb many times its own weight in liquids in a short period of time. A "foam", on the other hand, does not necessarily possess these specific absorption characteristics and may, for instance, be used for wound closure, e.g. to prevent infection and/or tissue adhesion, or for tissue regeneration purpose (cell ingrowth into pores). On the other hand, a foam may include such porous structures that are capable of absorbing fluids. Such foams are the subject of the present invention and are also referred to as absorbent foams (including sponges).

The term "packing" as used herein, refers to the action of placing an absorbent material in a suitable sized form (referred to as packs, tampons, plugs or dressings) in an antrum or other body cavity.

The term "antrum" as used herein, refers to a natural occurring body cavity, which may also be a lumen.

The term "biodegradable" as used herein, refers to the ability of a polymer to be acted upon biochemically in general by living cells or organisms or part of these systems, including hydrolysis, and to degrade and disintegrate into chemical or biochemical products.

The term "bioresorbable" as used herein, refers to the ability of being completely metabolized by the human or animal body.

The term "phase-separated polymer" as used herein, refers to a polymer comprising soft (amorphous) segments, as well as hard (crystalline) segments, the hard segment having a phase transition temperature of at least mammalian body temperatures (which is generally 37° C. for humans) and the phase-separated morphology being manifest when the foam prepared from such a polymer is applied in the human or animal body for a sufficient period of time. Also, the polymer placed under temperature conditions comparable to the human or animal body exhibits said phase-separated morphology. A phase separated polymer is characterised by the presence of at least two immiscible or partly miscible phases with a different morphology at normal environmental conditions. Within one material a rubber phase and a crystalline phase (at a temperature above the glass transition temperature of the amorphous phase and below the melting temperature of the crystalline phase) may be present or a glassy and a crystalline phase (at a temperature below the glass transition temperature of the amorphous phase). Also at least two amorphous phases can be present at a temperature between the two phase transitions e.g. one glassy and one rubbery phase. At a temperature above the highest phase transition which is either a melting- or glass transition temperature, the liquid and rubbery or the two rubbery phases, respectively, can form a phase mixed morphology or they can still be immiscible. Immiscible liquid and/or rubbery phases usually results in a polymer with a phase separated morphology without the initial desired mechanical properties at normal environmental conditions.

The term "amorphous" as used herein, refers to segments present in the polymer of the invention with at least one glass transition temperature below the temperature of the antrums or other cavities of the human or animal body into which the foam is packed, and may also refer to a combination of an amorphous and crystalline segment which is completely amorphous when packed in the human or animal body. For example, PEG in a pre-polymer may be crystalline in pure form, but may be amorphous when comprised in the R segment of a polyurethane of the formula (I) or (II). Longer PEG segments may also be partly crystalline when comprised in the R segment of a polyurethane of the formula (I) or (II), but will become amorphous ("dissolves") when placed in contact with water. Therefore such longer PEG segments are part of the soft segment of the phase separated polymer of the formulas (I) or (II), whereas the hard segment should remain crystalline in nature to provide sufficient support to a foam in the wet and packed state for, at least, a certain period of time.

The term "crystalline" as used herein, refers to segments, present in the polymer of the invention, that are crystalline when packed in the human or animal body, i.e., that have a melting temperature above the temperature of the antrums or other cavities of the human or animal body into which the foam is packed.

A "hydrophilic segment" as used herein, refers to a segment comprising at least one, preferably at least two, more preferably at least three hydrophilic groups such as can be provided for instance by C—O—C, or ether, linkages. A hydrophilic segment may thus be provided by a polyether segment. A hydrophilic segment may also be provided by polypeptide, poly(vinyl alcohol), poly(vinylpyrrolidone) or poly(hydroxymethylmethacrylate). A hydrophilic segment is preferably derived form polyalkyleneglycol, such as polyethyleneglycol, polypropyleneglycol, or polybutyleneglycol. The preferred hydrophilic segment is a polyethyleneglycol (PEG) segment.

The term "segment" as used herein, refers to a polymeric structure of any length. In the art of polymer technology a long polymeric structure is often referred to as a block, whereas a short polymeric structure is often referred to as a segment. Both these conventional meanings are understood to be comprised in the term "segment" as used herein.

The biodegradable absorbent foam according to the present invention has the advantage that it does not have to be mechanically removed after being applied to an antrum, such as the nasal cavity, since it degrades over time. The time before the material starts to loose its mechanical properties and disintegrates allows to the surrounding tissue to heal. Meanwhile, the tissue is supported and retained in position by a foam of the invention due to its mechanical properties and the foam is capable of absorbing considerable amounts of fluid. After a certain period of time, the foam degrades and disintegrates. In this way damage to the surrounding tissue is prevented, or only occurs to a very limited extent.

The characteristics of this foam material are for a large part brought about by the nature of the polymeric material from which the foam is prepared. This polymeric material comprises a phase-separated polymer consisting of an amorphous segment and a crystalline segment. Without wishing to be bound by theory, it is believed that this phase-separation of the various soft (amorphous) and hard (crystalline) segments attributes to the specific mechanical properties of the foam material, such as its resilience.

A foam of the present invention comprises, i.a. a polymer wherein urethane, urea or amide bonds are provided. These bonds are denoted $Z^1$-$Z^4$ and optionally $Q^1$ and $Q^2$, in the formulas defined hereinabove and constitute part of the crystalline segment of the polymer of the invention provided that $q \neq 0$. Since these hard, crystalline segments are chemically incompatible with amorphous aliphatic polyesters, polyetheresters, polyethers, polyanhydride or polycarbonates comprised in the segment R, phase separation in the polymer occurs. The hard segments crystallize and form strong hydrogen bonds with other hard segments resulting into physical cross-links.

Furthermore, the biodegradability of the material is accomplished by the provision of enzymatically cleavable or hydrolysable bonds in a polymer of the invention. For the material to be biodegradable, several types of polymers known to the art may thus be comprised in a polymer of the invention. Such biodegradable polymers may include polymers with one or more ester, anhydride and/or carbonate hydrolysable moieties, optionally combined with ether moieties. Such groups are very suitable provided in the R element according to the formula (I) or (II) for a polymer for use in a foam of the invention, although the ether or ester moieties may also be comprised in the R' and/or R" elements of the crystalline segment. In the case that q is zero in polymers of formula (I) or in the case that there are no hydrogen-bond forming groups present in the copolymer, e.g. in polymers other than those of formula (I), i.e. such as in those of the formula (II), the phase separation of crystalline hard segment and amorphous soft segments is provided by incompatible polyether, polyester, polyanhydride and/or polycarbonate groups, at least one phase being crystalline, comprised for example through R in formula (I) or otherwise.

The polymers of the invention are believed to degrade by the hydrolysis and/or enzymatic mechanism of the ester, carbonate, anhydride, urethane, urea or amide linkages. The rate of degradation and other properties can be regulated by choosing the content and combination of these moieties in the final polymer.

Examples of synthetic biodegradable polymers that can be applied in the manufacturing of foams of the present invention are those based on polyesters, polyhydroxyacids, polylactones, polyetheresters, polycarbonates, polydioxanones, polyanhydrides, polyurethanes, polyester(ether)urethanes, polyurethane urea, polyamides, polyesteramides, poly-orthoesters, polyaminoacids, polyphosphonates and polyphosphazenes. The polymeric material may also be composed of mixtures of above components either as different building blocks of the copolymer or cross-linked polymer or as a blend of two or more (co)polymers.

For providing the foam material with absorbent characteristics, it has furthermore been found that the polymers used for the preparation of the foams of the present invention can be improved considerably by combination of the polymer with hydrophilic polymers or groups. This means that the above mentioned polymers are chemically combined with these hydrophilic groups, e.g. by incorporating hydrophilic polymers in the backbone or side-chains of the resulting polymers. Also a foam of the invention may comprise physical blends of biodegradable and hydrophilic polymers. Hydrophilic polymers or groups may be based on polyethers, polypeptides, poly(vinyl alcohol), poly(vinylpyrrolidone) or poly(hydroxymethylmethacrylate) (polyHEMA). The preferred hydrophilic polymer is a polyether, viz. a polymer or segment comprising at least one —C—O—C— group, because these compounds are easy to handle in chemical synthesis reactions. Moreover, these compounds are generally regarded safe (GRAS). The preferred polyether is polyethyleneglycol. The hydrophilic groups are part of the soft segment where they will increase the degradation rate of the ester, carbonate or anhydride groups under the conditions were the foams of the present invention are to be applied, and may additionally be part of the hard segment.

In particular the absorption capacity (amount of water uptake and rate thereof) and degradation behaviour can thus be controlled by incorporating during synthesis a suitable quantity of these hydrophilic polymers or groups. It is thus also possible to incorporate hydrophilic groups into the hard segment to increase the solubility and/or rate of degradation of the hard segment and thus shorten the time needed for complete degradation or resorption of the polymer, however, care should be taken that the hard segment provides the phase-separated polymer with sufficient resilience, even when wet.

From the above it is clear that, by proper selection of the soft and hard segments the period of time for biodegradation by enzymes and fluids of the human or animal body can be controlled, as well as the extent to which the material is degraded. Complete biodegradation will result in fragments that are small enough to be metabolised by the body. In a particular application of the material such as a nasal dressing, the degradation products of this material, in smaller or larger fragments, are cleared either via the digestive channel or via bodily orifices, such as the nose, nostrils, before they are degraded in to fragments that can be metabolized by the body. An absorbent foam according to the invention may suitably comprise polymeric materials that are not completely bioresorbable, but only biodegradable to an extent that allows clearance, in smaller or larger fragments, from the cavity where they were applied.

The time until fragmentation of the foam starts (which is the time until the mechanical strength of the foam is lost upon putting a slight pressure, although the foam might still show some elastic behaviour) may vary from a few hours to several weeks but is preferably from 1 hr-21 days, more preferably from 6 hrs to 5 days, the preferred time being depending on the site and purpose of the application. Complete fragmentation (no cohesion of the material and/or foam structure) and disappearance is preferably from 1-10 days, more preferably from 2-5 days in the event that the foam has to be cleared from the wound after a temporary use (e.g. a nasal packing). In case the foam is used in an artificially made cavity such as a dental implant for closing an oro-antral communication or as a haemostatic sponge, the time until fragmentation starts is preferably within 1 and 14 days. During this time or afterwards, tissue in-growth in the highly porous foam material can take place followed by complete degradation and absorption of the degradation products by the body. The time until the material is completely degraded and absorbed will depend on the type of building blocks of the polymer and the rate of hydrolytic and/or enzymatic degradation thereof. This may vary from several weeks or months to a few years.

In the oral cavity, e.g. after tooth extraction, an absorbent foam according to the invention may biodegrade more slowly, so as to allow growth of new tissue. In dental surgery, for instance, situations may occur in which a completely bioresorbable material is required. For instance, during extraction of an element of the maxilla, a communication between the oral cavity and the maxillary sinus may be created. Such an oro-antral communication is usually closed by a surgical procedure in which a mucosal flap is sutured over the wound. Closure with a bioresorbable foam of the present invention has the advantage of lower discomfort to the patient. Closure with an bioresorbable foam of the invention protects the maxillary sinus from being infected.

Furthermore the absorbent foam absorbs blood by its haemostatic and porous structure and displays sufficient strength to remain properly positioned during the time of healing of the wound. New tissue may grow into the absorbent foam. After a certain period, which may be controlled by proper selection of the polymer used for its manufacture, the biodegradable absorbent foam of the invention will degrade to mere residue and will eventually be completely metabolized by the body.

Such a completely metabolizable absorbent foam pertains to another advantage of the present invention. If the bioresorbable absorbent foam of the invention is applied in the human or animal body (for example a haemostatic laparotomy sponge or as an implant) and is left in place without the intention of ever being removed therefrom, the degradation products have to be metabolised by the body. Therefore, polymeric material from which an absorbent foam according to the present invention is prepared is preferably chosen such that it is completely bio-absorbable. Application of such bio-absorbable absorbent foam in surgical intervention has the advantage that the material does not necessarily have to be removed after surgery, but that it can be left in place. It is an aspect of the present invention to provide a biodegradable synthetic absorbent foam for use in the human or animal body.

The materials according to the present invention have the advantage that they will disintegrate in a period of time of several days, or at maximum several weeks. This reduces the incidence of complications induced by the removal of haemostats and increases patient's convenience. According to the invention a material is provided having superior mechanical properties, including excellent elasticity and support to the surrounding tissue, which is important in stanching the flow of blood and/or keeping the tissue in its position. Yet the material is capable of disintegrating rapidly, followed by clearance from a body cavity were it is applied. This combination of features cannot be arrived at by using conventional biodegradable materials of animal derived origin. The elastic properties (as well as the maintenance thereof upon application) are required to support the wound sufficiently to arrest bleeding and/or prevent tissue adhesion.

A foam of the present invention may have a density of $0.01$-$0.2$ $g/cm^3$, preferably of $0.02$-$0.07$ $g/cm^3$. Furthermore, a foam of the present invention may have a porosity of 85-99%, preferably from 92-98%, even more preferably from 95-98%. A foam of the present invention has sufficient fluid absorption capacity at body temperature.

The fluid absorption capacity is mainly determined by the capillary absorption of water into the pores, due to the presence of the hydrophilic nature of the polymer and the pore geometry. The pores of the foam must be small enough to retain the fluids. The amount of water absorbed in a highly porous foam is almost equal for a range of porosities, since the total pore volume of the foam is hardly affected. This means that the capacity measured in g water/g polymer is dependent on the density of the foam: e.g. doubling of the density from $0.01$ $gram/cm^3$ to $0.02$ $gram/cm^3$ will give half the absorption capacity (g/g). Therefore, the absorption capacity is measured as the amount of water (g) absorbed per volume ($cm^3$), which is preferably $0.5$-$0.99$ $g/cm^3$, more preferably $0.75$-$0.97$ $g/cm^3$. For example, a hydrophilic polyurethane foam as described in the examples with a density of $0.04$ $g/cm^3$ and having a porosity of 96.4% has an absorption capacity of 0.8 g of water per $cm^3$. This is similar to a capacity of 20 grams of water per gram of polymer material.

In nose bleeding applications, the uptake of fluids should be very rapid in order to generate some limited pressure in the wound area as to stop the bleeding. The fully loaded foam should still provide sufficient support to the wound tissue.

Within a short period of time the amount of absorbed liquids should be maximal, preferably within 20 minutes with squeezing of the foam in the liquid. The degree of swelling of the foam should be low: the foam preferably should keep it's dimensions when saturated. A swelling of less than 10%, preferably less than 5%, more preferably less than 2% should be observed. This is desired in case the foam is pre-wetted before insertion of the antrum or cavity. Swelling means in this case, the maximum increase of volume of the foam compared to the volume of a dry foam.

A foam of the present invention has mechanical properties such as a sufficient resilience or elasticity, which are maintained under "wet" conditions, i.e., when the foam is in contact with bodily fluids, including e.g. purulent material. Both the solubility of the polymer blocks in water and the molecular weight of the polymer are important for these aspects as will be elucidated later with some examples.

A foam of the present invention is hydrophilic, viz. shows a good wettability. A good wettability may be defined as having a contact angle (for water droplets) that is substantially lower than 80°, preferably lower than 40°, more preferably substantially zero degrees.

Preferably, the foam of the invention is provided in one piece, since this enables an easy way of manufacturing. However, several pieces can be used at the same time in order to fill a cavity with sufficient material to absorb the blood and arrest the bleeding. The foam can be made in any possible shape and size by the use of e.g. casting methods well known in the art.

The foam of the present invention may be in the form of e.g. plugs (packs, tampons or dressings) or porous sheets. The sheets may subsequently be rolled into a plug or tube).

A foam for filling a nasal cavity may very suitably have a thickness of 1-50 mm, preferably of 8-15 mm, more preferably 12-15 mm. The width of the foam is preferably 10-30 mm, more preferably 15-20 mm. Its length is typically several tens of mm, e.g. 20 to 90 mm, or more.

FIG. 1 shows an example of a shape of a foam according to the present invention, which can be used e.g. post-surgically as a nasal packing or for treating of epistaxis, having a thickness (h) of e.g. 10-15 mm; a width (w) of e.g. 15-20 mm; and a length (l) of 35 to 85 mm. The depicted shape and size are preferred for filling a nasal cavity and give good compression to the mucosal tissue.

According to the present invention foams, suitable for packing antrums or other cavities of the human or animal body, comprise a phase-separated polymer consisting of an amorphous segment and a crystalline segment and wherein at least the amorphous segment comprises a hydrophilic segment. According to the present invention the polymer on which the absorbent foam is based is a phase-separated linear polymer or a chemically cross-linked polymer.

A phase separated morphology results in a polymer having at least two phase transitions in one polymer as indicated by two melting temperatures, two glass transition temperatures or one melting point and one glass transition temperature.

It was found that the above-mentioned requirements can be very suitably obtained by providing a phase-separated synthetic polymer comprising —C(O)—O— groups in the backbone of the polymer. Preferably the polymer is a polyurethane (—NH—C(O)—O—), polyester (—C(O)—O—), polyanhydride (—C(O)—O—C(O)—) or polycarbonate (—O—C(O)—O—) based polymer, viz. a polymer wherein a nitrogen atom (polyurethane based), carbon atom (polyester or polyanhydride based) or oxygen atom (polycarbonate) is connected to the C-atom of said —C(O)—O— groups together with either an aliphatic carbon atom next to the O-atom (polyurethane, polyester and polycarbonate) or a carbonyl group (polyanhydride).

The backbone of the polymer used in accordance with the present invention is preferably formed of a copolymer, which comprises two or more different units, at least one selected from the urethane, urea or amide moieties, and at least one selected from the group of ester, anhydride or carbonate moieties combined with an ether moiety.

A very suitable copolymer for application as a hydrophilic biodegradable foam is a polyether(ester)urethane.

In another preferred embodiment, the foams comprising phase separated polyesters, polyanhydrides and combinations thereof with polycarbonate and polyether groups may be either random or block copolymers in which a block can contain one or more of the above mentioned moieties. Preferably, block copolymers are used, in particular multi-block segmented copolymers in which both a crystalline and an amorphous phase are present. Physical blends of a phase separated polymer with another phase separated or a single phase amorphous (co)polymer may be used in formation of foams with intermediate properties. By varying the combination of polymers, the foam properties can be tuned such as rate of degradation, hydrophilic and mechanical properties. For example, a foam of a blend of a polyesterurethane and a co-polyester with a similar composition as the soft segment of the polyurethane gives properties intermediate of those of the two components, due to the compatibility of the polymers. Furthermore, poly(ether)esterurethanes with different soft segment composition, the soft segments being either compatible or not, and with the same type of hard segment may be mixed and produced into a foam with intermediate properties.

High molecular weights are not required to obtain a polymer or foam with good initial mechanical properties. Preferred intrinsic viscosities lie between 0.5 and 4 dl/g, depending on the type of polymer that is used. For instance, for certain polyurethanes, an intrinsic viscosity of 0.6 dl/g can still give a highly porous foam with good mechanical properties. Phase-separated polyurethanes according to formula (I) with molecular weights of the pre-polymer of 2000 may have an initial elastic modulus varying from 30-120 MPa and a tensile strength of 10-45 MPa. The elongation at break varies from 500-1200% (measured on polymeric films).

Alternatively, synthetic polymers may be used based on polyamides (viz. polymers containing —NH—C(O)— units in the backbone) or polyurea (viz. polymers containing —NH—C(O)—NH— units in the backbone). Combinations of urethane, urea and/or amide linkages in the above mentioned structures are also possible. A very suitable copolymer for application in a hydrophilic biodegradable foam is a polyether(ester)urethane.

The phase separated polymers can be semi-crystalline homopolymers, block copolymers or multi-block segmented copolymers. At least one phase has preferably a transition temperature higher than 37° C. The segment or block with the highest transition temperature is referred to as the "hard" block, while the segment or block with the lowest transition temperature is referred to as the "soft" block. The hard block may consist of urethane, urea, amide, polyester or polyanhydride groups, preferably with a phase transition from a crystalline to liquid state, or a combination of these elements. The soft block preferably comprises an amorphous polyester, poly-anhydride or poly-carbonate with a glass transition temperature of 37° C. or below. Such a temperature makes a foam very suitable for use in the human body.

The pliability, compressibility and elasticity of the foam can be controlled by selecting the ratio between hard and soft blocks as well as their composition in the polymer. The content and composition of the hard block contributes to the initial strength of the foam in the wet and dry condition. Therefore, the content and composition of the hard block must be chosen such that sufficient initial strength of the foam in the wet and dry condition is obtained. In order to produce a foam of which the structure is maintained after wetting, the hard blocks preferably has a less hydrophilic character than the soft blocks. In order to achieve a faster dissolution of the polymer and rapid loss of materials properties, which is in some cases advantageous, a more hydrophilic hard block may be selected.

A phase-separated polymer according to the invention may be represented by the formula:

$$—[R-Q^1[—R'—Z^1—[R''—Z^2—R'—Z^3]_p—R''—Z^4]—R'-Q^2]-_n \quad (I),$$

wherein R, R', R", $Z^1$-$Z^4$, $Q^1$, $Q^2$, n, p and q are as defined above.

In this formula, —R— represents the soft segment, or a combination of a soft segment and a hard segment.

Further, the part $-Q^1[—R'—Z^1—[R''—Z^2—R'—Z^3]_p—R''—Z^4]_q—R'-Q^2$ represents the crystalline or hard segment, the composition of which is largely determined by the method of manufacturing of this segment of the polymer (see below). In such a polymer, the bonds are preferably such that they provide for the possibility of hydrogen bonding between individual polymer strands. Therefore, $Q^1$ and $Q^2$ are preferably selected from urea, urethane or amide. When q is 0 in this part, i.e. when a polymer of the formula —R-$Q^1$-R'-$Q^2$- is comprised in a foam of the invention, the phase-separated morphology is best achieved in the polymer by providing one crystalline R element together with one amorphous R element, i.e. by the provision if two different R elements, since the element -$Q^1$-R'-$Q^2$- itself usually does not provide sufficient crystalline properties. When q=0 the choice for $Q^1$ and $Q^2$ is less critical.

R is selected from one or more aliphatic polyesters, polyetheresters, polyethers, polyanhydrides and/or polycarbonates, and at least one R comprises a hydrophilic segment, R' and R" are independently $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O in the alkylene chain. When no hydrophilic segment is present in the part of the polymer that is associated with the aliphatic polyether, polyester, polyanhydride and/or polycarbonate, a suitable biodegradable and hydrophilic polymer for the manufacture of a foam of the invention may be provided by selecting at least one R element to be a polyether. Alternatively, the hydrophilic segment may also be comprised in the R' or R" element, although this is not preferred. A hydrophilic segment is always present in the soft segment.

The R element, derived form the pre-polymer A-R-A', may suitably comprise an amorphous polyester, obtained, for instance, by ring opening polymerization of cyclic lactones such as lactide (L,D or L/D), glycolide, ε-caprolactone, δ-valerolactone, trimethylene carbonate, tetramethylene carbonate, 1,5-dioxepane-2-one or para-dioxanone. These polyester pre-polymers preferably contain hydroxyl end-groups obtained by using 1,4-butanediol or polyethyleneglycol as an initiator.

R' is $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O in the alkylene chain. R' is derived from a diisocyanate of the formula O=C=N—R'—N=C=O (formula IV), such as alkanediisocyanate, preferably 1,4-butanediisocyanate (BDI).

R" is $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O in the alkylene chain. R" is derived from a compound of the formula B—R"—B' (formula V), wherein B and B' are independently selected from hydroxyl, carboxyl or amine, preferably 1,4-butanediol (BDO).

$Z^1$-$Z^4$ may be urea, amide or urethane, preferably urethane. In that case, the polymer of formula (I) is a polyurethane. The structure of the polymer of the invention will be more apparent when understanding the methods for its manufacture. In a phase separated polymer of the invention, preferably at least 4 hydrogen bond forming groups such as amide, urea and urethane are present in a row in the crystalline segment. Other bonds ($Q^1$ and/or $Q^2$) may also be carbonate, ester or anhydride. Therefore, R' is not necessarily derived from a diisocyanate component such as the compound of the formula (IV). Moreover, the group R' in —$Z^2$—R'—$Z^3$— may be different or similar to R' in -$Q^1$-R'—$Z^1$— or —$Z^4$—R'-$Q^2$-.

Preferably, in a polymer of the invention, the hard segments have a uniform block length. This means that within one polymer according to formula (I), the values for p and q are constant. A uniform block length also implies very good phase-separation and can be obtained by different chain-extending methods. A phase separated polymer with the highest degree of phase separation, is i.a. obtained by chain-extending the soft segment forming pre-polymer R (hydroxyl terminated in case R is derived by ring opening polymerization of cyclic lactones and using a diol as the initiator) with a diisocyanate chain-extender.

Diisocyanate chain-extenders that are suitable for obtaining polymers with uniform hard segments and with suitable mechanical properties are e.g. diisocyanate-end-capped diol components, obtained i.a. by reacting one equivalent of an R" comprising diol, such as 1,4-butanediol (BDO) with two equivalents of the R'-comprising diisocyanate, such as 1,4-butanediisocyanate (BDI). This results in a compound of the formula:

$$O=C=N—R'—Z^1—R''—Z^2—R'—N=C=O \quad (VI)$$

In the case the diol is 1,4-butanediol (BDO) and the diisocyanate is 1,4-butanediisocyanate, this '3-block' chain-extender, or intermediate diisocyanate complex, is named BDI-BDO-BDI and will, when reacted to the compound of the formula (III), result in a polymer according to the formula (I) wherein p is 0 and q is 1 and the hard segment comprises the segment sequence R'—R"—R'.

A polyurethane according to formula (I) wherein p is 1 and q is 1, may be obtained by reacting two equivalents of an R" comprising diol, such as 1,4-butanediol (BDO) with one equivalent of the R'-comprising diisocyanate, such as 1,4-butanediisocyanate (BDI) and end-capping one equivalent of the thus formed BDO-BDI-BDO reaction product with two equivalents of 1,4-butanediisocyanate (BDI). This results in a '5-block' chain-extender, or intermediate diisocyanate complex, according to the formula:

$$O=C=N—R'—Z^1—R''—Z^2—R'—Z^3—R''—Z^4—R'—N=C=O \quad (VIII).$$

When 4-butanediisocyanate (BDI) and 1,4-butanediol (BDO) are used, this compound is shortly addressed with BDI-BDO-BDI-BDO-BDI. Such hard block segments provide for phase-separated polyurethane polymers from which very advantageous foams can be prepared, i.e. foams with very advantageous properties.

A phase-separated polyurethane suitable for preparing a foam of the invention can also be obtained by a method in which a di-hydroxy terminated pre-polymer is first reacted with an excess of a diisocyanate, resulting in an isocyanate end-capped pre-polymer. Subsequent chain-extension may occur by reacting the isocyanate end-capped pre-polymer with a) a diol compound of the formula (V), or with b) another intermediate compound, such as can for example be obtained by reacting one equivalent of a diisocyanate according to the formula (IV) with two equivalents of a diol of the formula (V), to prepare a compound of the formula:

$$B—R''—Z^1—R'—Z^2—R''B' \quad (VII).$$

An example of such a compound (VII) is the reaction product BDO-BDI-BDO.

Reacting the isocyanate end-capped pre-polymer with the compound of the formula (VII) will result in a phase-separated polyurethane of uniform block length and with p=1 and q=1, whereas the direct chain extension of the isocyanate end-capped pre-polymer with a diol compound of the formula (V) will result in a phase-separated polyurethane of uniform block length wherein and p=0 and q=1.

The degree of phase separation may in some cases be somewhat lower than is obtained by the chain-extension method described hereinabove, wherein the pre-polymer is not end-capped. I.e. performing a reaction between a pre-polymer and a diisocyanate and chain extending with e.g. a diol according to the formula (V) results in a polymer wherein the phase-separated is sub optimal to that of a polymer obtained by reacting a diisocyanate-end-capped chain extender with a pre-polymer according to the formula (III). The degree of phase-separation may be lower in the polymers that are obtained by reacting the diol component according to the formula (V) as the chain-extender. A diol according to the formula (V) can cause trans-esterification of the labile ester groups of the pre-polymer so that the uniformity of the hard block is lost. The sensitivity of the ester group towards trans-esterification is very dependent on the chemical environment of this group. For instance, ester groups in poly-(lactide) segments are much more labile than ester groups from poly(caprolactone) segments. Consequently, polyurethanes based on poly-(lactide) segments will have a less phase separated structure than those based on poly(caprolactone) segments. A diisocyanate chain-extender does not cause this side-reaction, resulting in an even better phase-separation.

A method for preparing a phase-separated biodegradable polymer according to the invention, thus comprises the steps of reacting one or more pre-polymers of the formula:

A-R-A' (III), with one or more diisocyanates of the formula:

O=C=N—R'—N=C=O (IV)

and optionally one or more chain extenders of the formula:

B—R"—B' (V)

wherein R, R' and R" are as defined in formula (I), and A, A', B and B' are independently selected from hydroxyl, carboxyl or amine. Preferable, the above compounds (III), (IV) and (V) are reacted in a solvent, more preferably in 1,4-dioxane or trioxane.

The reaction between the pre-polymer of the formula (III) end-capped with the diisocyanate of the formula (IV) and the chain extender of formula (V), or the reaction between either one of the intermediate diisocyanate complexes described above and the pre-polymer of the formula (III) is generally carried out at a temperature between 15° C. and 90° C., preferably between 55° C. and 75° C., more preferably between 60° C. and 70° C.

The polymer of the present invention may be produced in bulk, or, more preferably, it may be produced in a solvent. A very suitable such solvent is 1,4-dioxane or trioxane. 1,4-Dioxane is the preferred solvent since it is advantageously cheap. Preferably, the pre-polymer and diisocyanates are reacted in bulk, whereas the chain extending reaction is preferably performed in 1,4-dioxane.

The initial rate of degradation of the foam depends on the composition of the polymer soft segment; the initial molecular weight (obtained by measuring the intrinsic viscosity) as well as the composition determine the time between the start of the gradual fragmentation and the loss of mechanical properties. Excellent results have been obtained using a polyurethane of formula (I) with p=1 and q=1, and R' and R" both being (—CH$_2$—)$_4$. As aliphatic polyethers, polyesters, polyanhydrides and/or polycarbonates for use in a polymer of the present invention, any compounds may be employed. Preferably, R is a pre-polymer containing an amorphous polyester, obtained by ring opening polymerisation of cyclic lactones such as lactide (L,D or L/D), glycolide, ε-caprolactone, δ-valerolactone, trimethylene carbonate, tetramethylenecarbonate, 1,5-dioxepane-2-one or para-dioxanone and mixtures thereof. Most preferably, the pre-polymer is a combination of lactide and ε-caprolactone and with a molecular weight of 2000. The monomer ratio is such that the poly(caprolactone) sequences do not crystallise. Preferably, the ε-caprolactone content is less than 60%, more preferably between 30 and 60%, most preferably it is about 50%. The polyester is combined with polyethyleneglycol in a weight content of 1-80%, preferably 5-60%, more preferably 20-50%, most preferably about 50%. It is preferred that the polyethyleneglycol is present as an initiator of the pre-polymer.

Very suitable foams can be produced from polymers wherein R is an amorphous polyester derived from lactide and ε-caprolactone, with a molecular weight between 1 000 and 4 000 and even more preferably from polymers wherein said amorphous polyester comprises about 25 wt. % lactide, about 25 wt. % ε-caprolactone and about 50 wt. % of polyethyleneglycol.

The molecular weight of the pre-polymer is preferably about 1500-2000. This may be obtained by using a diol, e.g. 1,4-butanediol as an initiator or a polyethyleneglycol (PEG) with molecular weight of 1000. The first obtained pre-polymer may then combined with the desired amount of PEG as a second pre-polymer. The PEG initiated pre-polymer already contains at least 50% (w/w) PEG and can also be mixed with another pre-polymer or PEG to adjust the total amount of PEG in the pre-polymer.

The polymerization reaction between the two types of pre-polymers as employed in a method of the invention for preparing an absorbent foam may comprise such reactions as known in the art. Polyesters, polycarbonates, polyamides or polyanhydrides can be made by methods such as ring opening polymerisation and/or condensation reactions, followed by the chain-extending (or polymerization) process. Polyurethanes may for instance be made by a condensation reaction of isocyanates with hydroxyl groups, by means of chain-extending of pre-polymers. Polyurea are made by a similar condensation of an isocyanate with an amine group.

Alternatively, different pre-polymers and chain extenders can be coupled by reaction of activated functional groups (such as carboxylic acid, hydroxyl or amine). Several methods for activating functional groups are known in the art. Examples are the uses of N-hydroxysuccinimide and derivatives, carbonyldiimidazole, aldehydes, maleimides, dicycloxexyl carbodiimide (DCC). The advantage of the use of such coupling agents is that high temperatures that are usually applied in condensation reactions are avoided. Therefore, in another embodiment of the invention, a foam may be prepared by a method comprising preparing a phase-separated biodegradable polymer of the formula (II) by reacting a mixture of at least two compounds according to formula (III), of which at least a first such compound comprises an R group representing an amorphous segment comprising a hydrophilic segment, and of which at least a second such compound comprises an R group representing a crystalline segment, said method further comprising providing said mixture with a compound of the formula (V) and performing a chain extension reaction between said compounds in the presence of an activator such as N-hydroxysuccinimide or derivatives, carbonyldiimidazole, aldehydes, maleimides or dicycloxexyl carbodiimide (DCC).

Alternatively, a foam may be prepared by a method comprising preparing a phase-separated biodegradable polymer of the formula (II) by reacting a mixture of at least two compounds according to formula (III), of which at least a first such compound comprises an R group representing an amorphous segment comprising a hydrophilic segment, and of which at least a second such compound comprises an R group representing a crystalline segment and performing a chain extension reaction in the presence of an activator such as N-hydroxysuccinimide or derivatives, carbonyldiimidazole, aldehydes, maleimides or dicycloxexyl carbodiimide (DCC). Such extension reactions in the presence of an activator are well known in the art.

Because the presence of an R' or R" group is not necessary in a polymer suitable for the manufacture of a foam of the invention, two different pre-polymers according to the formula III (comprising R groups) may thus be joint together directly. The provision is that at least one R group is amorphous and one R group is crystalline. The joining together of such pre-polymers may be achieved by providing such compounds in the form of diols or dicarboxylic acids as described earlier. However, when the presence of isocyanates is, for instance, to be avoided in a reaction mixture or the presence of urethanes in a polymer of the invention is to be reduced, use of a diisocyanate according to the formula (IV) may be prevented by coupling the pre-polymers comprising an R group by alternative methods.

A very suitable alternative method may comprise the use of so called activators like N-hydroxysuccinimide, carbonyldiimidazole, aldehyde, maleimide or dicycloxexyl carbodiimide (DCC) or derivatives thereof. Such activators are capable of chemically bonding pre-polymers comprising an R group that are similar to the compounds of the formula (III), to form a polymer of the formula (II), wherein $Q^1$ or $Q^2$ may comprise different groups as described. $Q^1$ or $Q^2$ carbonate groups may, for instance, be created in the polymer of the formula (II) by performing a condensation-reaction with phosgene. $Q^1$ or $Q^2$ anhydride groups may be introduced by performing a coupling-reaction between carboxylic acid end-groups of such pre-polymers.

Therefore, a polymer according to the formula (I) or (II) may also suitably be performed by using coupling reactions with activators, instead of reactions involving, for example, diols and diisocyanates in a method of the invention described earlier. The $Q^1$ and $Q^2$ groups may suitably be prepared as an ester, an anhydride or a carbonate by selecting the chain extender and the pre-polymer such that their terminal reactive groups comprise the proper combination of for example, carboxylic acid, alcohol or chlorocarbonate groups (e.g. a compound of the formula (III) Cl—(CO)—O—R—). Thus, in alternative methods for preparing a polymer of the invention for the manufacturing of a foam of the invention, a compound of the formula (III) may be coupled or reacted with another compound of the formula (III) in the presence of an activator, provided that one compound is amorphous and one is crystalline. Also, a compound of the formula (III) may be coupled or reacted with another compound of the formula (III) in the presence of a compound of the formula (IV), in which case no activator is necessary, since the isocyanate will provide the necessary energy. Also, a compound of the formula (III) may be coupled or reacted with another compound of the formula (III) in the presence of a compound of the formula (V), in which case an activator is again necessary. The skilled person will understand what alternative methods and building blocks may be used to arrive at the phase-separated polymers suitable for the manufacturing of foams according to the present invention.

Foam material according to the present invention is preferably prepared by a freeze-drying process. As stated, the advantage of producing a polymer of the present invention in a solvent is that a very advantageous starting material is thus provided for the preparation of a foam of the invention. A very suitable route of preparation comprises producing the polymer in a suitable solvent, followed by cooling, during which cooling step the polymeric material precipitates or crystallizes and the solvent crystallizes, and finally a freeze-drying step. In this respect it is noted that 1,4-dioxane is a very suitable solvent. By preparing the polymer in the solvent, the process step of dissolving the polymer in the solvent may be avoided and a very efficient manufacturing process for biodegradable absorbent foams according to the present invention is thereby obtained.

By using a freeze drying method, the foam can be made directly from the polymer solution, which simplifies the process (isolation of the polymer by precipitation from the solution is not necessary). In case multi-functional chain-extenders or pre-polymers are used (more than 2 reactive groups) the cross-linking reaction can take place in solution in the mould, after which the solvent is frozen and sublimated. Furthermore, the porosity of the foam can easily be changed. By addition of non-solvents, the foam structure and homogeneity can be tuned. The solvent can be completely removed, i.e. so that residual content is lower than acceptable limit, by freeze drying.

It is preferred to carry out the polymerisation reaction either in the bulk or in a 1,4-dioxane solution. Usually in the art, polyurethane chain-extending reactions are carried out in very polar solvents such as dimethyl sulfoxide (DMSO), N-methylpyrrolidone (NMP) or dimethylformamide (DMF) examples of which are given in international patent nr. WO99/64491. Polar solvents are mainly used because of the very good solubility properties of polyurethanes and other hydrogen-bond forming polymers in these solvents. In this way, high molecular weights can be obtained. Applying these solvents, requires an additional precipitation step of the polymer solution in a non-solvent such as water. Except for the fact that it is a time consuming step, it is also a disadvantage that the polymers have to be dried afterwards which might lead to early degradation or cross-linking reactions of the polymer. Furthermore, not all polymers are hydrolytically stable in this type of solvents. In case a (very) hydrophilic polymer is made (as is the case with some of the polymers of this invention), a precipitation step into water is undesirable. The polymer will swell and may be difficult to isolate and dry without some degradation taking place.

Using 1,4-dioxane as a solvent offers many advantages: polymers with sufficient molecular weight are being formed; the polymerisation temperature and polymerisation time can generally be lower, which may lead to less side-reactions (e.g. trans-esterification) and a better phase separation; the initial pre-polymer concentration can be much lower than in e.g. DMSO (35% vs. 60% w/w), which makes the process better to control (e.g. viscosity of a solution can easily be monitored); foams of polymer networks can be made, the polymer solution can be diluted to the desired concentration after which the solution can be poured directly into the mould, frozen and freeze dried. If desired, the dioxane solution can be precipitated into water or organic non-solvents. Furthermore, polymer solutions in dioxane can be easily formed into solid materials such as polymeric films and sheets by evaporation of the solvent at rather low temperatures.

In another process for preparing a foam suitable for packing antrums or other cavities of the human or animal body, the synthesis of the polymer is performed in the bulk and the foam is formed in situ upon formation of carbon dioxide by a chain-extending reaction of a diisocyanate molecule with a dicarboxylic acid or hydroxycarboxylic acid molecule and/or water, optionally in combination with reaction of a diol molecule (either a diol pre-polymer or diol chain-extender) to control the amount of liberated gas. This solvent-free method has been described in EP-A-1 138 336, but highly porous foams used as an absorbent dressing have not been disclosed.

Solvent-free produced foams based on poly(ether)ester urethanes of formula (I) can be obtained by reaction of a diisocyanate chain-extender group with a di-carboxylic acid or hydroxycarboxylic acid initiated pre-polymer optionally combined with a diol initiated pre-polymer or polyethyleneglycol.

In another method, the biodegradable soft segment is end-capped with 1,4-diisocyanate and the di-carboxylic acid or hydroxycarboxylic acid molecule, a diol and/or water are the chain-extenders.

As stated earlier, foamed materials according to the present invention are preferably prepared by a freeze-drying process. An alternative method comprises the extrusion of porous sheet using a foaming agent such as low boiling liquids, solids or carbon dioxide. Such a method comprises providing a phase-separated biodegradable polymer and forming said polymer into a foam of the invention, for example, by using a blowing agent in a extrusion method as known in the art. Such an extrusion method may for instance comprise the melting of said polymer and the extrusion of the melt thus formed into a foam by the aid of a gas, preferably a gas such as carbon dioxide.

The foams manufactured by methods of the present invention may be sterilized e.g. with ethylene oxide without loss of shape or volume and without significant decrease in molecular weight. The foams may be impregnated with various substances, that can be released at a controlled rate upon wetting, which can make these foams also suitable for drug delivery purposes. Furthermore, loading with radiopaque fillers and haemostatic components is also possible.

The foams of the present invention are characterised by having suitable elastic properties such as needed for application as wound dressing applications or other biomedical foam uses in accordance with the present invention. A foam of the invention can very suitably be used as a haemostatic sponge, such as a laparotomy sponge. Also, it may be used as a nasal dressing for the treatment of epistaxis, as a dressing for the outer ear and as a post surgery wound dressing to prevent from tissue adhesion.

Alternatively, due to its biodegradability and optionally bio-resorbability, a foam of the invention may be used for drug delivery purposes.

A foam of the invention is very suitable for use in dental surgery and for closing an oro-antral communication after tooth extraction. Therefore in another aspect, the present invention relates to the use of a foam according to the invention as a haemostatic sponge, as a wound dressing material, as a packing for antrums or other cavities of the human or animal body or as a drug delivery vehicle.

In a final aspect, the present invention relates to the use of a phase-separated biodegradable polymer according to the invention, for the manufacture of a foam according to the invention.

The invention will now be exemplified by the following, non-limiting examples.

EXAMPLES

Analysis Methods and Characterization of Polymers and Building Blocks:

The following analysis methods were used in all examples, unless indicated otherwise.

The intrinsic viscosity was measured in chloroform or 1,4-dioxane at 25° C. using an Ubbelohde viscometer (according to ISO standard 1628-1).

Monomer conversion, pre-polymer and chain-extender composition were determined using $^1$H-NMR at 300 MHz in solutions in deuterated chloroform.

Thermal properties were determined using a TA Instruments-Q1000 MDSC, 5-10 mg samples being heated at a rate of 10° C. per minute, cooled down at a rate of 20° C. per minute and heated again at a rate of 10° C. per minute.

Mechanical properties were determined on thin films with an Instron 4301 tensile tester. The films were measured at room temperature at a crosshead speed of 10 mm/minute. The ultimate tensile strength, the elongation at break and the initial modulus were determined from these measurements.

Purification and/or drying of monomers and glassware is according to previously published methods and is sufficient to obtain polymers with the desired properties.

Porosities were calculated by measuring the dimensions and the dry weight of a foam, assuming a density of the polyurethane of 1.1 g/cm$^3$.

The absorption capacity of a foam was measured by calculating the wet/dry ratio of a foam after exposing to an excess of water (with or without squeezing/soaking of the foam) as a function of time at 37° C.

The degree of swelling was calculated by measuring the dimensions of the foam before and after saturation with water as a function of time.

Example 1: (50/50) Glycolide-ε-caprolactone Pre-Polymer (Mn=2000)

The pre-polymer was synthesized by ring opening polymerization of ε-caprolactone and glycolide in a 50/50 (mol/mol) ratio using 1,4-butanediol as initiator and stannous octoate as catalyst (M/I=10000). After reaction at 130° C. for 6 days, $^1$H-NMR shows complete monomer conversion. Thermal analysis shows a completely amorphous pre-polymer with a glass transition temperature between −40 and −35° C.

Example 2: (50/50 Glycolide-ε-caprolactone) Pre-Polymer Initiated with PEG1000 (Mn=2000)

The pre-polymer was synthesized by ring opening polymerization of ε-caprolactone and glycolide in a 50/50 (mol/mol) ratio using polyethyleneglycol (PEG) with a molecular weight of 1000 as initiator and stannous octoate as catalyst (M/I=10000). PEG is dried under vacuum at 50° C. during at least 8 hours, where after the monomers and catalyst are added. The mixture is reacted at 140° C. for 6 days, $^1$H-NMR shows complete monomer conversion. Thermal analysis shows a semi-crystalline pre-polymer with a glass transition temperature between −50° C. and −40° C., a crystallisation peak between −10° C. and 0° C. and a melting peak of the PEG segment of 15-20° C.

Example 3: (20/40/40) Lactide-Glycolide-ε-caprolactone Pre-Polymer (Mn=2000)

The pre-polymer was synthesized according to the method of example 1 by ring opening polymerization of ε-caprolactone, glycolide and lactide in a 40/40/20 (mol/mo/mol) ratio using 1,4-butanediol as initiator and stannous octoate as catalyst (M/I=10000). Thermal analysis shows a completely amorphous pre-polymer with a glass transition temperature between −22° C. and −23° C.

Example 4: (20/40/40 Lactide-Glycolide-ε-caprolactone) Pre-Polymer Initiated with PEG1000 (Mn=2000)

The pre-polymer was synthesized according to the method of example 2 by ring opening polymerization of ε-caprolactone, glycolide and lactide in a 40/40/20 (mol/mol/mol) ratio using polyethyleneglycol (PEG) with a molecular weight of 1000 as initiator and stannous octoate as catalyst (M/I=10000). Thermal analysis shows a semi-crystalline pre-polymer with a glass transition temperature of −44° C., and a small melting peak of the PEG segment of 22° C. In the second DSC run, the Tg is −47° C., a crystallisation peak at −15° C. and a melting peak at 23° C. are observed.

Example 5: (50/50 Lactide-ε-caprolactone) Pre-Polymer Initiated with PEG1000 (Mn=2000)

The pre-polymer was synthesized by the same method as described in example 2 by using DL-Lactide instead of glycolide. Stannous octoate was used as a catalyst (MA=10000-15000). The mixture is reacted at 140° C. for 14 days, after which $^1$H-NMR shows complete monomer conversion.

Example 6: Synthesis of (3/1) ((50/50)Glycolide-ε-caprolactone)/PEG1000 (w/w) Based Polyurethane with BDI.BDO.BDI.BDO.BDI Hard Segment in 1,4-dioxane The BDOBDIBDO chain-extender was prepared according to the method given in international application PCT/NL99/00352 and was subsequently purified, such that a purity of 98% was obtained. The melting point of the chain-extender was 97° C. In the first step of the polyurethane synthesis, the hydroxyl terminated pre-polymers of example 1 and 2 in a 1:1 molar ratio is end-capped with a 5 to 6 fold excess of 1,4-butanediisocyanate (BDI) under mechanical stirring. After reaction at 62° C. for 4 hours, the excess BDI was removed by distillation under reduced pressure ($1*10^{-3}$ mbar) at 65° C. until the theoretical molecular weight of the end-capped pre-polymer is reached.

In the next step of the polymerization, the thus obtained macro-diisocyanate pre-polymer is chain extended at 65° C. with the BDO-BDI-BDO chain extender using 1,4-dioxane as solvent (35% w/w). The chain-extender is added in small portions to the well stirred pre-polymer solution. When the solution becomes viscous, the mixture is diluted with small amounts of 1,4-dioxane. This procedure is repeated until no increase of viscosity is observed. The polymer solution is diluted to the desired concentration with 1,4-dioxane. A small amount of water or c-hexane is added. The solution can be precipitated into water or organic solvents, it can be concentrated by evaporation of the solvent and be dried in vacuum or it can be frozen and subsequently freeze dried. An intrinsic viscosity of a freeze dried polymer between 1 and 2 dl/g can easily be obtained under these conditions, although polymers with lower molecular weight might be useful for some applications.

Example 7: Synthesis of (3/1) ((20/40/40)Lactide-glycolide-ε-caprolactone)/PEG1000 (w/w) Based Polyurethane with BDI.BDO.BDI.BDO.BDI Hard Segment in 1,4-dioxane A polymerisation reaction according to the method of example 6 with pre-polymers of examples 3 and 4 gives a polymer with similar molecular weights.

Example 8: Synthesis of (1/1) ((50/50)Lactide-ε-caprolactone)/PEG1000 (w/w) Based Polyurethane with BDI.BDO.BDI.BDO.BDI Hard Segment in 1,4-dioxane A polymerisation reaction according to the method of example 6 with a pre-polymer of example 5 gives a polymer with similar molecular weights.

Example 9: Preparation of Glycolide Based Foams

The polymer solution of Example 6 is diluted to 2.5 wt. % in dioxane (gram of polymer in polymer/solvent mixture) and 2 wt. % of water (gram of water/gram of solution) is added. The solution is filtered over a 3 μm filter and poured into a mould. The solution is frozen at −20° C. after which it is freeze dried at a pressure of 3 mbar, followed by drying at $1*10^{-3}$ mbar until constant weight. The foams can be sterilized with ethyleneoxide. By the same method, foams of polymer of example 7 can be produced. The foams are stored below 4° C. The calculated porosity of the foams prepared this way has an average of 96.4%.

Example 10: Preparation of Lactide Based Foams

The polymer solution of Example 8 is diluted to 1.8 wt. % in dioxane (gram of polymer in polymer/solvent mixture) and 2 wt. % of c-hexane (gram of water/gram of solution) is added. The solution is filtered over a 3 μm filter and poured into a mould. The solution is frozen at −20° C. after which it is freeze dried at a pressure of 3 mbar, followed by drying at $1*10^{-3}$ mbar until constant weight. The foams can be sterilized with ethyleneoxide. The foams are stored below 4° C. The calculated porosity of the foams prepared this way has an average of 97.2%. By the same method, foams of 3.5 wt. % can be produced with an average porosity of 95%. The foams of this example are particularly useful as a nasal dressing.

Results and Discussion

Thermal, mechanical, absorption and degradation behavior of polymers of examples 6 and 7 and foams thereof are determined.

Figure 2:
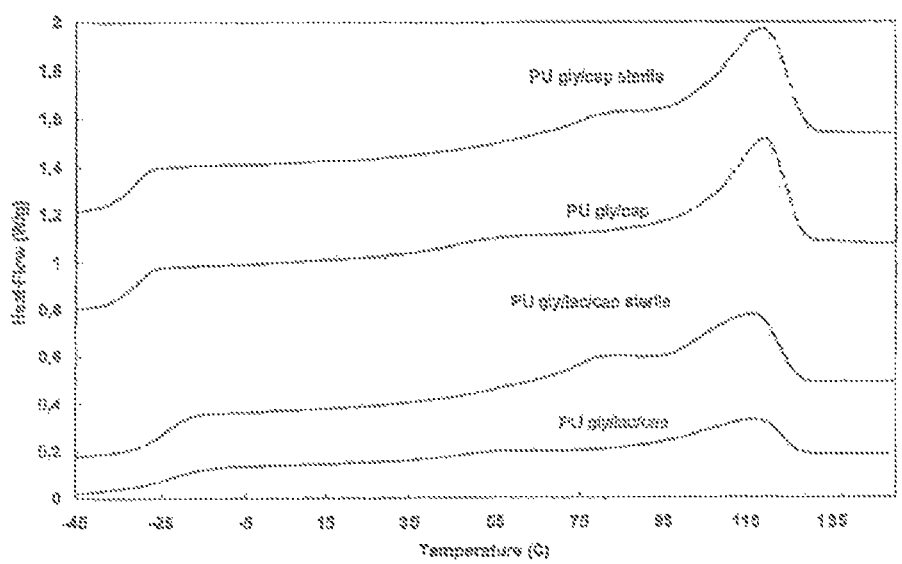
FIG. 2 shows the thermal behaviour of foams of polyethyleneglycol-containing polyurethanes of the invention with different pre-polymer composition, sterile and non-sterile, as described in the results and discussion to the examples.

Upon EtO sterilization, the intrinsic viscosity of foams may decrease with about 0.1 dl/g, while the shape and dimensions of the foams are retained. FIG. 2 shows the thermal behavior of polyurethane foams before and after sterilization. The thermal properties are changed somewhat (shift of phase transitions) as a result of annealing of the polymer during the sterilization process at 40-50° C. (3-4 days in total). The hard segment gives a broad melting peak, which is caused by a complex formed by the hydrogen atoms of the urethane segments and the ether groups of PEG.

A porosity of the foam of 96.4% is calculated, which is about 1% less than the theoretical calculated porosity based on the 2.5 wt % solution (97.7%). This is mainly due to some shrinkage of the foam during freeze drying. Mechanical properties of the polymer are measured on thin films. To this end, the foams of example 9 made of polymers of example 6 and 7 are dissolved in chloroform and the solution is poured into a petri-dish. After evaporation of the solvent and drying in vacuum at 40° C., a transparent film is obtained. The results are shown in Table 1. The difference in strength may be explained by a lower molecular weight of the lactide containing polymer. Mechanical properties of the foams are not measured quantitatively, but their very good elastic properties can be related to the materials properties measured on films.

TABLE 1

Mechanical properties of PEG containing PU's with different pre-polymer composition

| Gly/lac/cap ratio | 50/0/50 | 40/20/40 |
|---|---|---|
| Modulus (MPa) | 57 | 67 |
| Tensile strength(MPa) | 18 | 12 |
| Strain at break (%) | 750 | 520 |

Table 2 shows the absorption capacity and the swelling behavior of foams of polymers of examples 6 and 7. The tested foams are cylindrical shaped with a weight of about 100 mg and a porosity of 96.4% (based on a 2.5 wt % solution in dioxane). The foams are soaked in a Sorenson buffer solution (pH=7.4) at 37° C. and left there for 2 weeks. Immediately after soaking (by repetitive squeezing of the foam in the liquid) the maximum amount of water is absorbed (measured after 10 minutes). The foam absorbs 20-24 times its own weight and is independent of the size and shape of the foam.

After 14 days, the foam has not collapsed, but upon shaking, the foam fragmentizes into small particles. The dimensions of the foam are hardly changed during the time exposed to the buffer solution. An irregular change of dimensions during 14 days (measured as the change of diameter of the foam) is observed as a result of inaccurate measurements. Overall, the dimensions of the wet foam are increased with less than 3% compared to the dry foam. For comparison, the absorption capacity of Spongostan®, a gelatin based wound dressing, is 40 times its dry weight. However, the material swells and looses its mechanical strength almost immediately.

Figure 3:
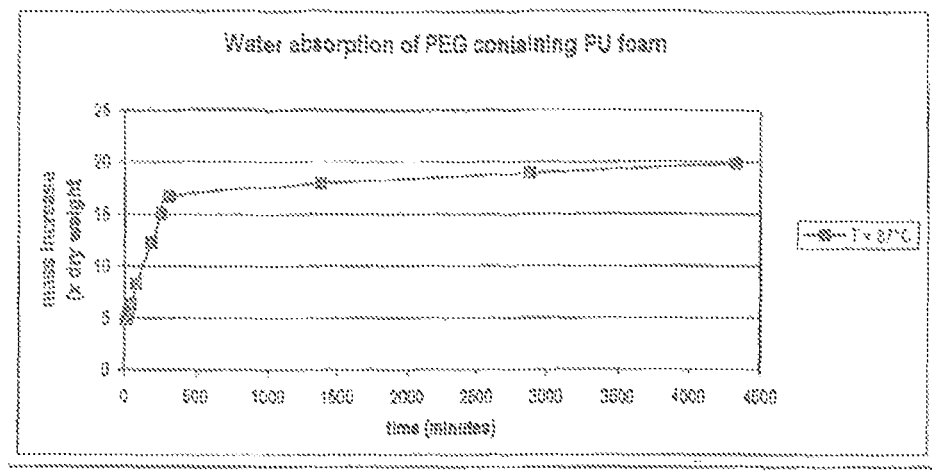
FIG. 3 shows the water absorption capacity of foam prepared from a (3/1) ((50/50)glycolide-ε-caprolactone)/PEG1000 (w/w) based polyurethane, as described in the results and discussion to the examples.

FIG. 3 shows the water absorption capacity of a foam with the shape and dimensions of FIG. 1 at 37° C. and without soaking the foam. The porosity is the same as the foams of Table 2 and its weight is about 700 mg. It takes about 5 hours until the absorption is leveling of to a value of 20 times the dry weight of the foams, which is a much longer time than when the foam is squeezed in the liquid. The absorption behavior is determined completely by the hydrophilic and capillary properties of the foam. The actual use of the foam (e.g. as a nasal dressing) will require compression of the foam to insert it into the wound. Therefore, the initial absorption capacity as shown in Table 2 will be most important. Similar absorption tests carried out at 21° C. gives a comparable rate of absorption, which might be important if the foam is pre-wetted before use.

Figure 4:
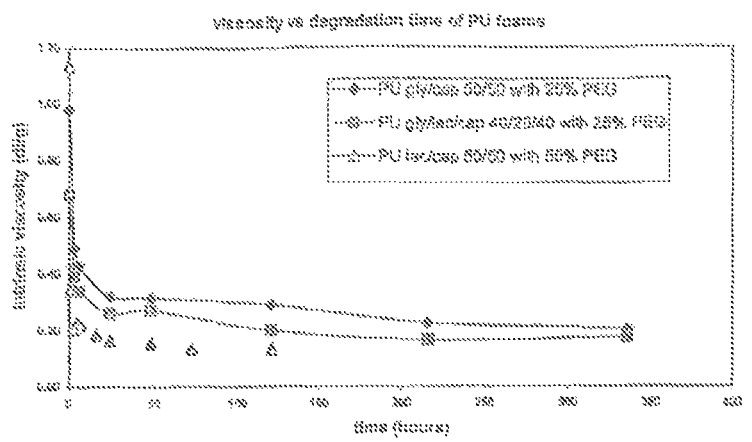
FIG. 4 shows the intrinsic viscosity of three PU foams vs. their degradation time at 37° C., as described in the results and discussion to the examples.

An in vitro degradation study of foams of polymers of example 6 and 7 with a 96.4% porosity have been carried out during a period of 14 days. During this time, the absorption behavior, the change of molecular weight and the change of mechanical properties were measured as a function of time. The absorption behavior has already been discussed. The intrinsic viscosity is initially decreasing very rapidly. In 3-5 hours the intrinsic viscosity is dropped with about 50% of the initial value; after that it is leveling of to an almost constant value. This is a result of chain scission in the polyester pre-polymer, caused by the presence of hydrophilic ether moieties. FIG. 4 shows the decrease of the intrinsic viscosity as a function of time of the two PU foams of example 9, and that of the lactide based foam with a 97.3% porosity and containing 50% PEG in the pre-polymer of example 10. The replacement of part of the glycolide and caprolactone by lactide does not have a large influence on the degradation behavior. The presence of 50% PEG instead of 25% PEG in the pre-polymer and/or the replacement of all glycolide by lactide seems to increase the initial degradation rate. Within one hour, the intrinsic viscosity has dropped to about ⅓ of the initial value. The time until fragmentation of the lactide foams starts is therefore somewhat shorter than that of the glycolide based foams. The very fast degradation of these foams is possibly also the result of the weak ester linkage between the PEG segment and the lactide derived monomer. The initial rate of degradation is in general somewhat lower for sterile foams with a similar composition; after 6-8 hours the intrinsic viscosity is half of the initial value.

Mechanical properties of the degrading foams are changing with the loss of molecular weight. For the PU foams of FIG. 4, the tear strength is lost at an intrinsic viscosity of about 0.4-0.5 dl/g. In case the foams are sterile, it takes a longer time until this point is arrived. Although the foam can be torn into pieces, the foams are still elastic. This means that even a partly degraded foam can put sufficient pressure on a wound to stop the bleeding of the wound or to prevent re-opening of the wound. After 1 day in a buffer solution at 37° C., the foam is fragmented under pressure and shaking. The foams of example 10 are very suitable for using in an application were a fast degradation and clearance of the foam is required such as a treating of epistaxis.

In general, the rate of degradation may be slowed down by choosing monomers that are more hydrolytically stable than glycolide and lactide. Also the amount of hydrophilic polymer and the way of incorporating in the polymer can have a large effect on the degradation properties. The presence of slowly degrading hard segments is, however, necessary to maintain the mechanical properties during application in a wound, which can be obtained with the polymers of the present invention.

Very suitable polyesters for use in the amorphous (R) segment of the polymer are based on lactide, glycolide and ε-caprolactone, preferably with a molecular weight of around 2000. Alternatively, the pre-polymer can be entirely based on lactide and ε-caprolactone. In such an alternative, the preferred ratio of the lactide and ε-caprolactone is about 1 mole/mole. Very favorable results have been obtained with such combinations wherein an amount of PEG of about 50 wt. % was provided as a pre-polymer initiator.

Very suitable polyethyleneglycol molecules for use in the present invention are those with a molecular weight of 150 to 4000 g/mol. Preferably, the molecular weight is between 600 and 2000 g/mol.

The polyethyleneglycol molecules can be incorporated into the amorphous segment pre-polymer in any suitable way, for example by ring-opening polymerization of cyclic monomers using polyethyleneglycol as an initiator or as a second pre-polymer combined with a polyester pre-polymer.

Polyethyleneglycol may thus be incorporated into the amorphous segment, to yield amorphous segment with between 1-80 wt. %, more preferably 10-60 wt. %, even more preferably 20-50 wt. % of polyethyleneglycol.

A foam of the invention may be loaded with radiopaque fillers in order to trace the material in the body.

Characteristically, a foam of the invention has a density of 0.01-0.2 g/cm$^3$, preferably of 0.02-0.07 g/cm$^3$. The porosity of the foam may suitably range form 85-99%, preferably from 92-98%, more preferably from 95-98%.

The absorption capacity of a foam of the invention at ambient temperatures (RT–37° C.) is in the range of 0.5-0.99 g/cm$^3$, more preferably 0.75-0.97 g/cm$^3$.

Figure 5:
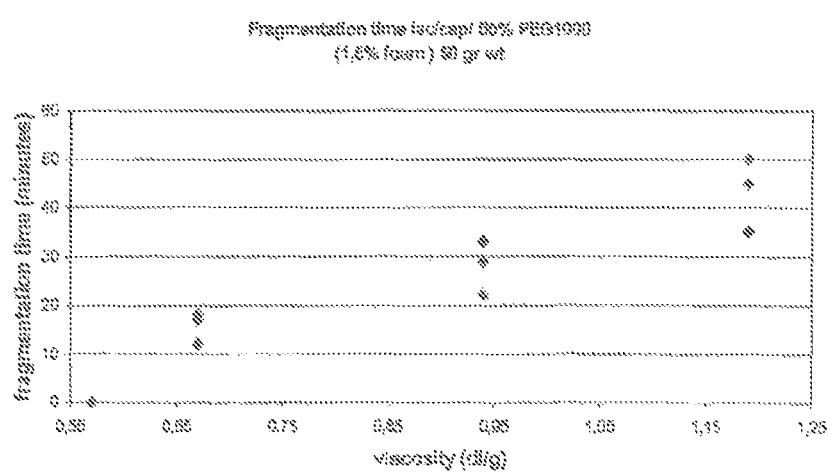
FIG. 5 shows the time until fragmentation vs the intrinsic viscosity of 1.8% foams based on (1/1) ((50/50)lactide-ε-caprolactone)/PEG1000 (w/w) in a buffer solution at 37° C. upon action of a weight of 50 grams as described in the results and discussion to the examples.

Generally, upon absorbing aqueous liquids, the biomedical foams of the prior art will rapidly loose either strength or elasticity. The foam of the present invention, however, exhibits a high mechanical strength when fully saturated with water at 37° C. as well as a maintained elasticity and shape. By selecting the type of polymer, the period during which the mechanical strength is maintained may be controlled. Preferably, the mechanical strength is eventually lost by the action of aqueous liquids on the foam. The fragmentation may however be delayed for a period of between 1 hr and 14 days, preferably between 6 hrs and 5 days. Rapid disintegration of a foam of the invention may be realized by using a polymer based on glycolide and lactide in combination with relatively high amounts of PEG, whereas disintegration may be for example be delayed by using monomers such as trimethylene carbonate and caprolactone, or reducing the amount of PEG in a glycolide/lactide based polymer. FIG. 5 shows the time until fragmentation vs the intrinsic viscosity of 1.8% (wt) foams, based on (1/1) ((50/50)lactide-ε-caprolactone)/PEG1000 (w/w) in a buffer solution at 37° C. upon action of a weight of 50 grams. The higher the intrinsic viscosity, the longer it takes until the foam starts to tear and fragment. Within one hour, the foams starts to fragment, which is much faster than foams based on glycolide-ε-caprolactone pre-polymers with 25% (w/w) PEG: 15-45 minutes vs 2-3.5 hrs, respectively, for comparable intrinsic viscosities. Foams of less than 1.5% (wt) polymer are fragmenting much faster than those of higher polymer concentration, the time also being dependent on the initial intrinsic viscosity. This proves that the mechanical and physical properties can be tuned by the polymer composition, content of hydrophilic component, initial intrinsic viscosity, foam porosity and also the mechanical force which is applied on the foam.

A foam according to the present invention may very suitably have an initial intrinsic viscosity of 0.5-4.0 dl/g. Generally, the loss of mechanical strength in the wet state is attained at an intrinsic viscosity of 0.4-0.5 dl/g, but may depend on the foam porosity. A foam of the present invention may comprise a physical blend of a hydrophilic phase-separated polymer with other biomedical biodegradable polymers. A very suitable polymer for the manufacture of a foam of the invention comprises a polyesterurethane combined with a an amorphous single phase (co)polyester or another polyesterurethane.

The foam of the present invention may be in the form of a plug (packs, tampons or dressings) or a sheet, said sheet preferably having a thickness of 1-50 mm, more preferably of 8-15 mm.

The foam of the invention may very suitably be used as a haemostatic sponge, such as a laparotomy sponge. Also, it may be used as a nasal dressing for the treatment of epistaxis, as a packing for the outer ear or as a post surgery wound dressing.

Due to its high absorption capacity and its controllable degradability by delayed disintegration, the foam of the invention may be used for drug delivery purposes. Preferably, a foam of the invention is used to prevent tissue adhesion. Also very suitable applications have been found in dental surgery, and specifically for closing an oroantral communication after tooth extraction.

Foams of the present invention were studied in a clinical trial in order to assess their properties as a synthetic fragmentable nasal dressing.

Patients with bilateral sinusitis or polyposis were randomized to left or right application of the fragmentable dressing (8×1.5×2 cm), the contra lateral nasal cavity received a standard dressing. The fragmentable dressings fragmented within 6 days whereafter they were drained via the mucus flow. Patients were recruited by 3 Dutch centres. 25 patients (54% male) were included, with a mean age of 47 years. In 71% of the cases it was the first clinical intervention for the pathology. 50% of the patients received medication after the procedure.

Figure 6:
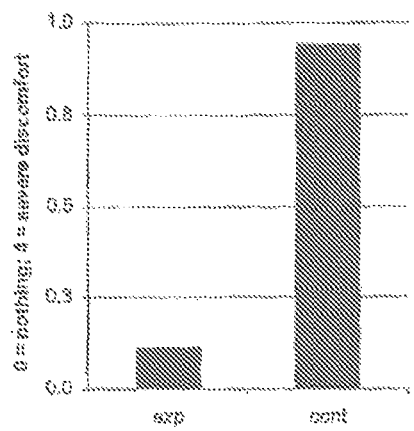
FIG. 6 shows the experienced patient discomfort during removal of a nasal dressing (Nasopore) of the experimental group (with a dressing according to a foam of the present invention) vs. the control group (a biodurable dressing).
Figure 7:
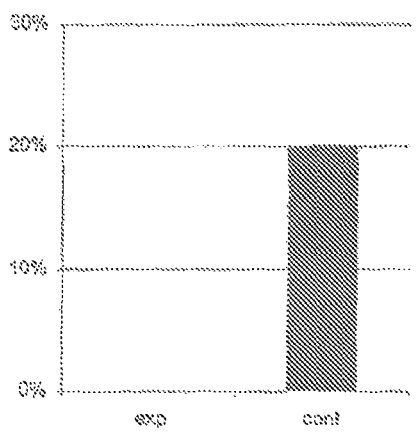
FIG. 7 shows the occurrence of nose bleedings during removal of a nasal dressing (Nasopore) of the experimental group (with a dressing according to a foam of the present invention) vs. the control group (a biodurable dressing).

The patients experienced discomfort when the durable dressing was removed which was not the case with the fragmentable dressing (FIG. 6). Final wound healing at 10 and 30 days was good and comparable between the groups. In 20% of the cases nose bleedings were observed at the control side, zero at the side with the new dressing (FIG. 7). These results indicate that the use of the new fragmentable nasal dressing is efficient and increases the comfort for the patient and lowers the risk of epistaxis, thereby avoiding new wounds in the nasal cavity as associated with the removal of non-fragmentable nasal dressings.

TABLE 2

Absorption behavior of foams of PEG containing PU's at 37° C. in buffer solution.

| Time in buffer | Mean Increase in weight (x dry weight) Foam A | Mean increase in weight (x dry weight) Foam B | Mean increase of foam diameter (%) Foam A | Mean increase in foam diameter (%) Foam B |
|---|---|---|---|---|
| 10-40 min | 21.8 | 23.7 | −1.56 | −0.40 |
| 3 hrs-14 days | 22.3 | 22.7 | 2.11 | 0.68 |

Foam A: polyurethane based on gly/cap (50/50) pre-polymer with 25 wt % PEG
Foam B: polyurethane based on gly/lac/cap (40/20/40) pre-polymer with 25 wt % PEG

What is claimed is:

1. A nasal packing comprising a phase-separated polymer including an amorphous segment and a crystalline segment, said polymer having the formula:

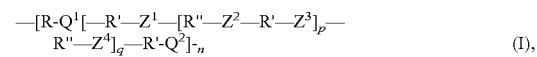

wherein:
    the amorphous segment comprises R, and at least one R comprises the reaction product of a polyethylene glycol initiator having a number average molecular weight of 600 to 2000 g/mol, lactide, and ε-caprolactone, such that said at least one R comprises a first polyester segment based on lactide and ε-caprolactone, a central hydrophilic segment based on polyethylene glycol, and a second polyester segment based on lactide and ε-caprolactone, wherein said at least one R comprises:

polyethylene glycol in a content of 10-60 wt. %, and lactide and ε-caprolactone in a content of 5-60 wt. %, R' and R" are independently $C_2$-$C_8$ alkylene, $Z^1$-$Z^4$ are each urethane, $Q^1$ and $Q^2$ are each urethane, n is an integer from 5-500, p and q are both 1, wherein said nasal packing has a complete fragmentation time ranging from 1 to 10 days.

2. The nasal packing according to claim 1, wherein R' is $(CH_2)_4$, R" is $(CH_2)_4$, or both R' and R" are $(CH_2)_4$.

3. The nasal packing according to claim 1, wherein said at least one R comprises lactide and ε-caprolactone in a content of 20-50 wt. %.

4. The nasal packing according to claim 1, wherein said at least one R comprises lactide and ε-caprolactone in a 1:1 molar ratio.

5. The nasal packing according to claim 1, characterized in that said nasal packing has a swellability of less than 5%, and a fluid absorption capacity of 1500-2500% based on a dry weight of said nasal packing.

6. The nasal packing according to claim 1, characterized in that said nasal packing has a fluid absorption capacity of 0.5-0.99 g/cm³ or a density of 0.01-0.2 g/cm³.

7. The nasal packing according to claim 1, wherein said at least one R comprises polyethylene glycol in a content of 20-50 wt. %.

8. The nasal packing according to claim 1, wherein said at least one R has a molecular weight between 1,000 and 4,000 and comprises about 25 w betide, about 25 wt. % ε-caprolactone, and about 50 wt. % of polyethyleneglycol.

9. The nasal packing according to claim 1, wherein said nasal packing has a porosity ranging from 85 to 99%.

10. The nasal packing according to claim 1 further comprising a drug substance.

11. The nasal packing according to claim 1 further comprising a haemostatic component.

12. The nasal packing according to claim 1, wherein said nasal packing has an initial elastic modulus of from 30-120 MPa and a tensile strength of 10-45 MPa.

13. The nasal packing according to claim 1, wherein said nasal packing has an initial elongation at break from 500-1200%.

14. The nasal packing according to claim 1, wherein the nasal packing has a thickness (h) of 10-15 mm; a width of 15-20 mm; and a length (l) of 35 to 85 mm.

15. A nasal packing comprising a phase-separated polymer including an amorphous segment and a crystalline segment, said polymer having the formula:

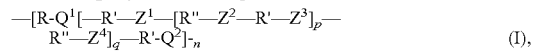

(I), wherein:

the amorphous segment comprises R, and at least one R comprises the reaction product of a polyethylene glycol initiator having a number average molecular weight of 600 to 2000 g/mol, lactide, and ε-caprolactone, such that said at least one R comprises a first polyester segment based on lactide and ε-caprolactone, a central hydrophilic segment comprising polyethylene glycol, and a second polyester segment based on lactide and ε-caprolactone, wherein said at least one R comprises:

polyethylene glycol in a content of 10-60 wt. %, and lactide and ε-caprolactone in a content of 5-60 wt. %, R' and R" are independently $C_2$-$C_8$ alkylene, optionally substituted with $C_1$-$C_{10}$ alkyl or $C_1$-$C_{10}$ alkyl groups substituted with protected S, N, P or O moieties and/or comprising S, N, P or O in the alkylene chain;

$Z^1$-$Z^4$ are independently amide, urea or urethane, $Q^1$ and $Q^2$ are independently urea, urethane, amide, carbonate, ester or anhydride, n is an integer from 5-500, p and q are both 1, wherein said nasal packing has a complete fragmentation time ranging from 1 to 10 days.

16. The nasal packing according to claim 15, wherein $Z^1$-$Z^4$ and $Q^1$ and $Q^2$ are each urethane.

17. The nasal packing according to claim 15, wherein said at least one R comprises lactide and ε-caprolactone in a content of 20-50 wt. %.

18. The nasal packing according to claim 15, wherein the nasal packing has a thickness (h) of 10-15 mm; a width of 15-20 mm; and a length (l) of 35 to 85 mm.

19. The nasal packing according to claim 15, wherein said at least one R comprises polyethylene glycol in a content of 20-50 wt. %.

* * * * *